(12) United States Patent
Crane et al.

(10) Patent No.: US 6,623,490 B1
(45) Date of Patent: Sep. 23, 2003

(54) CRANIAL BOLT

(75) Inventors: Barry C. Crane, Oxon (GB); Michael P. Irvine, Oxon (GB); David R. Markle, Berwyn, PA (US)

(73) Assignee: Diametrics Medical Limited, Bucks (GB)

( * ) Notice: Subject to any disclaimer, the term of this patent is extended or adjusted under 35 U.S.C. 154(b) by 0 days.

(21) Appl. No.: 09/762,634

(22) PCT Filed: Sep. 28, 1999

(86) PCT No.: PCT/GB99/03211

§ 371 (c)(1),
(2), (4) Date: Feb. 12, 2001

(87) PCT Pub. No.: WO00/20048

PCT Pub. Date: Apr. 13, 2000

(30) Foreign Application Priority Data

Oct. 2, 1998  (GB) ............................................. 9821575

(51) Int. Cl.[7] ................................................. A61F 11/00
(52) U.S. Cl. ..................................................... 606/108
(58) Field of Search .................. 606/108, 53, 213, 606/218; 604/104, 164.03, 164.04, 164.06, 264, 523, 533, 158

(56) References Cited

U.S. PATENT DOCUMENTS

| | | | |
|---|---|---|---|
| 4,629,451 A | | 12/1986 | Winters et al. |
| 4,903,707 A | * | 2/1990 | Knute et al. ................. 128/748 |
| 5,054,497 A | * | 10/1991 | Kapp et al. .................. 128/748 |
| 5,246,441 A | * | 9/1993 | Ross et al. ..................... 606/53 |
| 5,545,179 A | * | 8/1996 | Williamson, IV ........... 606/213 |
| 5,634,911 A | * | 6/1997 | Hermann et al. ............ 604/256 |
| 6,152,933 A | * | 11/2000 | Werp et al. .................. 606/130 |

FOREIGN PATENT DOCUMENTS

| | | |
|---|---|---|
| DE | 298 17 986 | 2/1999 |
| DE | 198 20 808 | 11/1999 |
| WO | 96/22798 | 8/1996 |

* cited by examiner

Primary Examiner—Eduardo C. Robert
(74) Attorney, Agent, or Firm—Merchant & Gould, P.C.

(57) ABSTRACT

A cranial bolt for connecting one or more elongate, flexible members such as catheters with the interior of the skull, wherein the bolt includes a hollow shank having one threaded end and a second end opposite the threaded end for receiving one or more elongate members. Each member is retained in the second end and communicates with a passageway in the shank extending to the threaded end.

16 Claims, 3 Drawing Sheets

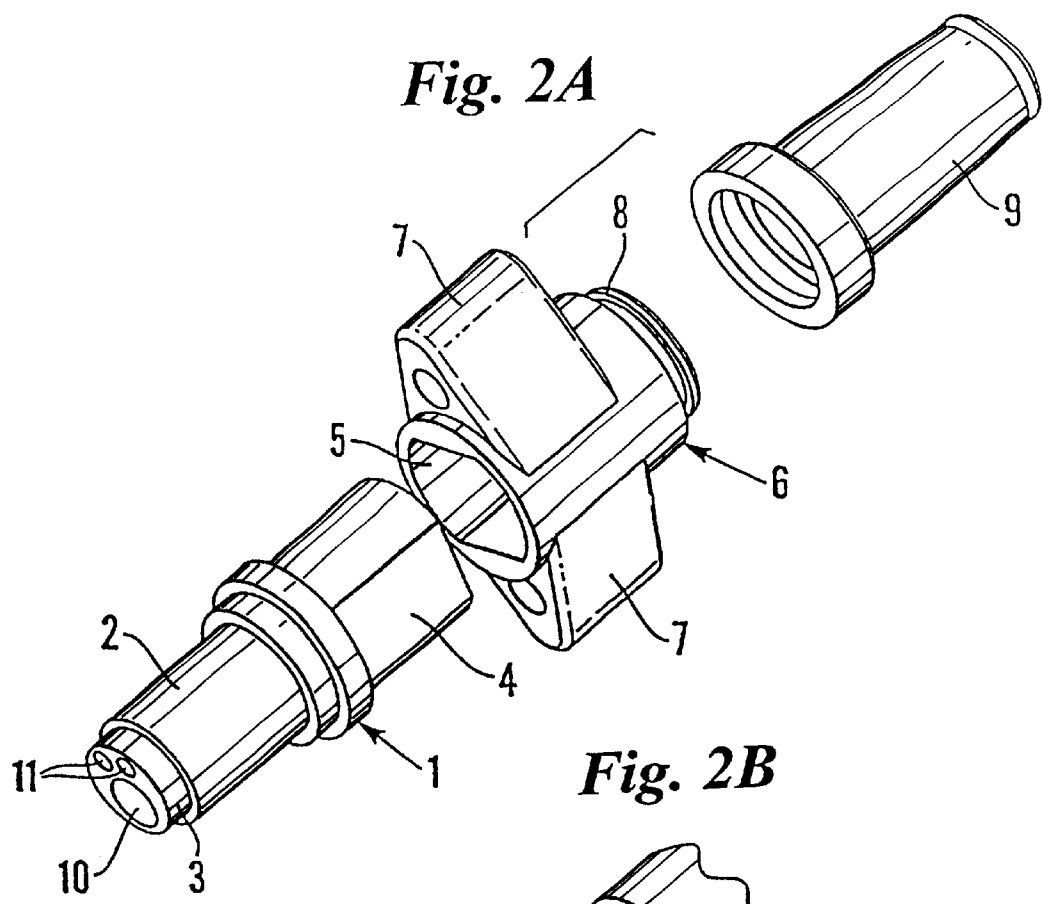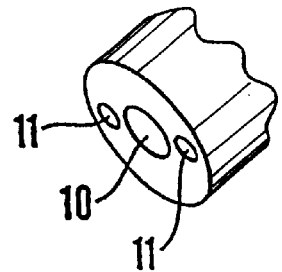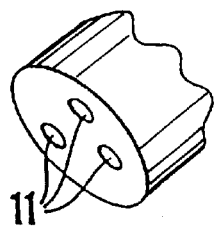

CRANIAL BOLT

TECHNICAL FIELD

This invention relates to cranial bolts or screws and systems for monitoring physiological functions in human and animal brains.

BACKGROUND

Cranial bolts are frequently used for temporarily securing a catheter to the skull, the catheter being used for monitoring intercranial pressure in the intensive care of patients who have suffered head injuries. In one procedure a catheter is introduced into the brain through a hollow bolt and the intercranial pressure measured by means of a sensor in the tip of the catheter. The catheter may be inserted into various parts of the brain. Where it is introduced into a cranial ventricle, the catheter may also be used to draw off cerebral spinal fluid (CSF) in order to alleviate pressure increases or to analyse samples of the CSF.

Existing cranial bolts are bulky and typically incorporate a Luer lock or other device for fixing the catheter securely to the bolt.

More recently interest has arisen in measuring a number of physiological parameters in the brain during intensive care. If a number of securing devices, such as Luer locks are incorporated in the bolt, it becomes even more bulky and awkward to use.

SUMMARY

It is now proposed to provide a cranial bolt in which one or more tubes (or a single multi-lumen catheter) are fixed directly into a hollow shank forming the body of the bolt and individual passageways are provided within the shank for passing probe(s) or tube(s) into desired positions in the brain.

According to one aspect of the invention there is provided a cranial bolt for connecting one or more elongate, flexible members, such as tubes, cables, filaments or the like, with the interior of the skull, said bolt comprising a hollow shank having one threaded end and a second end opposite said threaded end for receiving one or more elongate members, each said member being retained in said second end and communicating with a separate passageway in the shank extending to the threaded end.

Conveniently the tube or tubes or other elongate member are fixed into the end of the shank with adhesive.

It will be appreciated that instead of fixing a plurality of individual catheters into the second open end of the shank, a multi-lumen catheter could be fixed into the end of the shank and probes or smaller tubes fed through respective lumens and passageways into the brain. The term 'multi-lumen catheter' is used here in a broad sense and may comprise a bundle of individual tubes which are gathered together, e.g. by enclosing them in a common external sheath, or held together by a non-tubular gathering device such as a series of external rings or a spring-like coil. Alternatively, the multi-lumen catheter may be a catheter in which two or more lumens are extruded integrally so that externally the catheter appears to be a single tube. Whatever the particular construction selected, the individual lumens are split out of the assembly at the point where the catheter enters the shank and individual connections are made to passageways therein. Similarly, at the end of the assembly remote from the shank, the lumens are split out of the assembly and individual connections made to appropriate devices, e.g. via Luer locks.

Although the shank may be manufactured from plastics material, e.g. an engineering plastic such as polycarbonate, the shank is preferably made from metal. Some plastics are hard enough to cut a thread in the skull but metals do this more efficiently. Titanium or its alloys are preferred because they are non-magnetic and interfere less than other materials in magnetic scanning procedures. The bolts of the present invention are designed to make use of the minimum of metal.

In order to facilitate manipulation of the bolt and manually screwing the bolt into the skull while minimising the amount of metal employed in manufacturing the bolt, a metal shank is preferably received within a plastics body member which may be moulded with wings or other projections to permit the member to be gripped and the shank screwed more easily into a hole in the skull.

Preferably the shank is generally cylindrical and preferably formed with a central axial passageway and a further passageway or passageways disposed around the central passageway. The central passage preferably has a larger cross-section than the further passageways and may be used for example, for draining CSF fluid. The further passageways are preferably angled with respect to the central passageway. For example, they may be inclined at an angle between about 3 and 15° (such as about 5 to 10°) to the longitudinal axis of the shank.

In order to avoid the danger of the catheters kinking, particularly at or close to the point where they enter the shank, a kink-resistant catheter construction is preferred. Flexible tubes can be made kink-resistant by stiffening them with a spring 25, such as a coil spring. The spring may be metal or plastic but preferably is a tubular metal coil spring, and the wire from which it is made preferably has a generally flat cross-section. In order to minimise flow disturbance or contamination of fluids in the tube, the spring is preferably embedded or encapsulated in the wall of the tube or is sandwiched between coaxial tubes which form the catheter. Catheters such as described in U.S. Pat. Nos. 5380304 and 5700253 and in our U.S. patent application Ser. No. 09/093,934 are preferred, and their disclosure is specifically incorporated herein by reference.

BRIEF DESCRIPTION OF THE DRAWINGS

The invention is illustrated by the following specific description and accompanying drawings of cranial bolts in accordance with the invention, in which:

FIG. 2A is a perspective view of the same bolt in an exploded view, and FIG. 2B is a perspective, fragmented view of an alternate embodiment of the bolt, and FIG. 2C is a perspective, fragmented view of another alternate embodiment of the FIG. 3 is a schematic, partly in section, showing one way in which the bolt maybe fitted to a patients skull.

DETAILED DESCRIPTION

Figure 3:
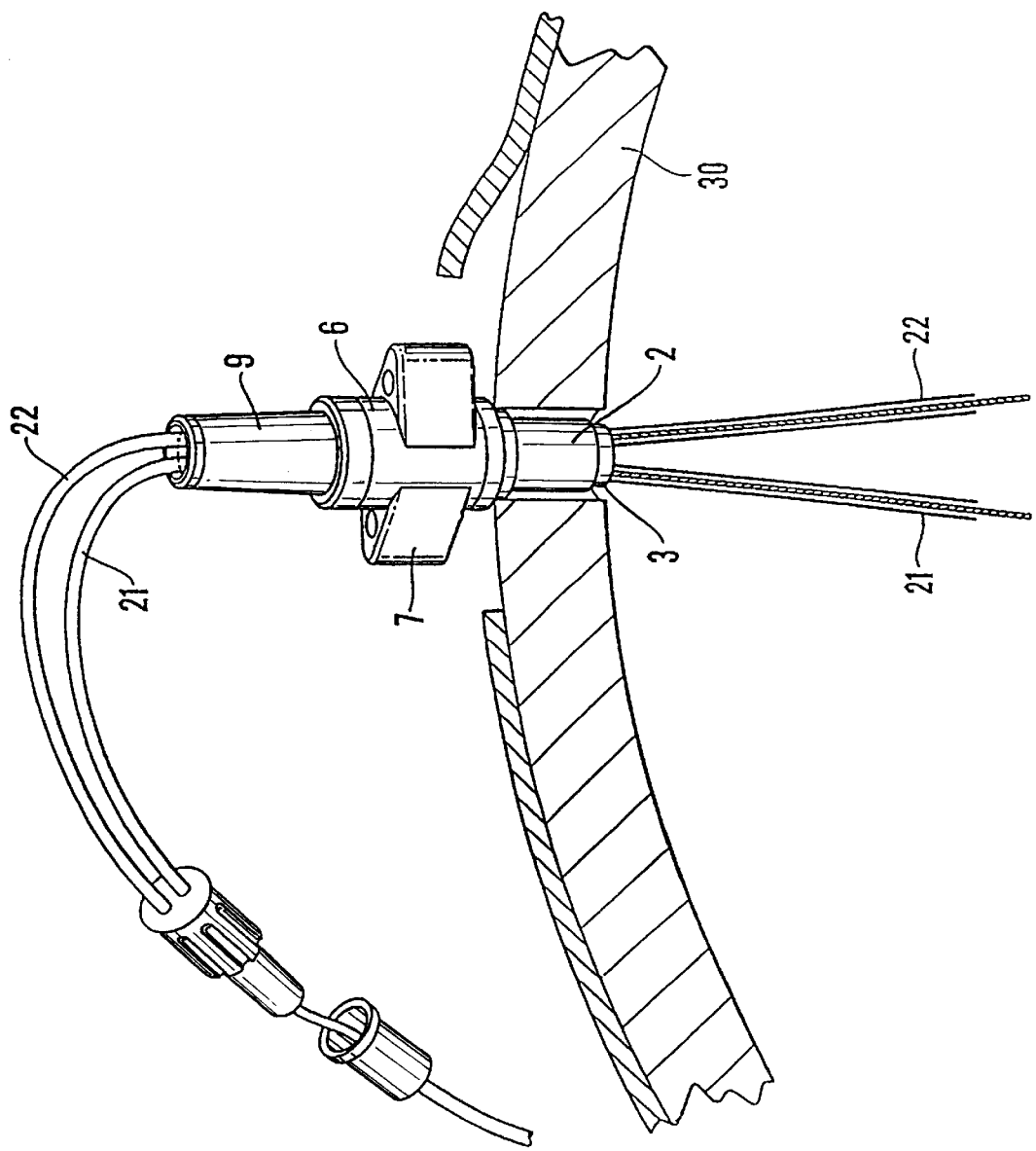

Referring to the drawings, the cranial bolt comprises a generally cylindrical shank 1 having a threaded lower end 2 for securing the bolt into a preformed hole in the skull 30, see FIG. 3. The distal end 3 of the shank has a smaller diameter than the threaded portion 2. This is to prevent the passageways within the shank being occluded by uncut portions of the skull at the inner end of the hole which has been cut to receive the threaded end. This arrangement may also avoid the need to ream the hole in the skull after cutting a hole of appropriate size to receive the shank and therefore simplify installation of the bolt. The shank 1 is formed at its upper end with a shaped profile 4 adopted to engage in a hole 5 in a plastic body member 6. Body member 6 is formed with wing-like projections 7 to facilitate screwing the threaded part 2 of the shank into a preformed hole in the skull. Body member 6 may be moulded separately from the shank or moulded onto the upper part 4. At its upper end, the body member 6 is formed with a part 8 which is connectible with a flexible collar 9. Collar 9 may be manufactured from a flexible, resilient plastics material and is a push fit onto the end part 8 of the shank or moulded in situ onto the end of the shank. The collar 9 helps to prevent chafing of the tubes 21,22.

Shank 1 is formed internally with a plurality of passageways. As seen best in FIG. 2A, one of the passageways 10 is larger than the other two 11. Passageway 10 preferably extends axially of the shank and is sized to house a drainage catheter. The passageways 11 may be disposed around the major passageways 10 and are designed to accommodate small catheters or probes for sensing parameters, such as oxygen concentration, carbon dioxide concentration, pH and temperature.

Figure 1:
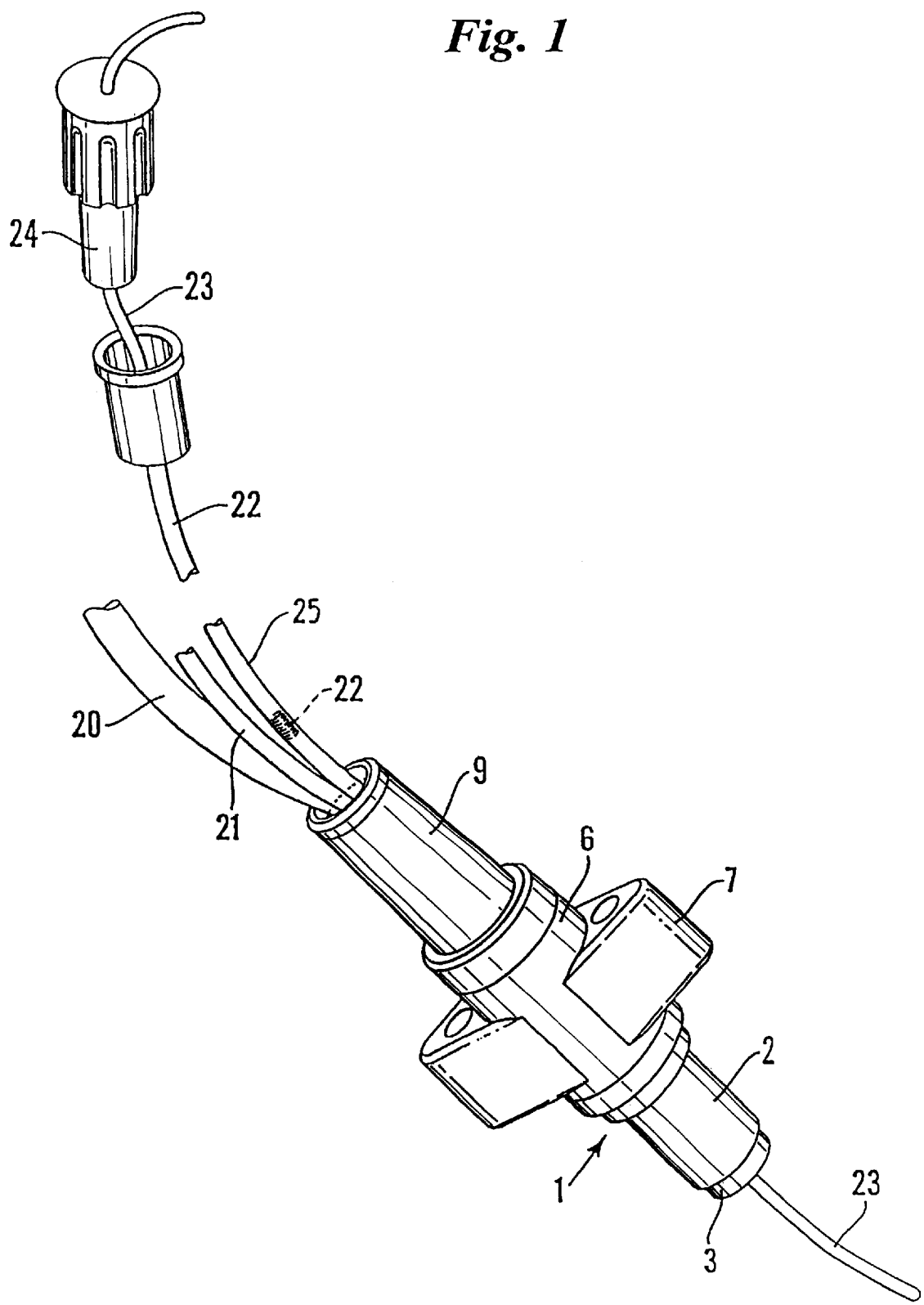
FIG. 1 is a perspective view of cranial bolt showing a member of catheters fixed to its receiving end.

FIG. 1 illustrates one way in which tubes 20, 21, 22 are grasped together and anchored to the bolt fixed into the extension piece 9, by fixing with adhesive into the shank portion. The distal ends of the tubes 20, 21, 22 may be sealed into the passageways 10, 11. The tubes 20, 21, 22 may constitute tubular guides through which sensors or smaller catheters are fed to the desired site. This is illustrated in FIG. 1 in which a catheter 23 is fed through tube 22, passes through the respective passageway in the shank and exits through the distal end of the shank. A Luer lock 24 is provided to maintain the catheter in the desired position after it has been located in the brain. A further alternative method of feeding probes or catheters into the bolt is to provide a multi-lumen tube which is fixed into the shank. Individual lumens are divided from the multi-lumen tube and aligned with passageways in the shank. Probes or catheters having diameters smaller than a lumen can then be fed into a respective lumen and passageway and into the brain through the distal end of the bolt. The tubes, 20, 21 and 22 are preferably kink-resistant, at least over the portion from the shank 1 to the Luer lock or locks 24.

Because the tubes or catheters are grouped together in the flexible collar 9 and extend axially of the shank, the bolt has a minimum lateral spread. This is advantageous because a bolt which is bulky and has in-feed catheters extending from the bolt in various directions is more likely to be knocked or displaced accidentally during nursing or handling the patient.

FIGS. 2B and 2C show alternate arrangements for the location of the passageways through the shank. In practice, it may be desirable to form the outer passageways 11 so that they are inclined at a small acute angle to the longitudinal axis of the shank. Preferably the angle is 3° to 15°, e.g. 4° to 8°.

FIG. 3 shows one method of fitting the cranial bolt into the skull 30. The scalp 31 is cut away for a sufficient distance to gain access to the skull 30 and a hole is cut in the skull 30 of a size which is just less than the diameter of the threaded part 2. The bolt can then be secured to the hole in the skull 30, by securing the threaded part 2 into the skull 30. Once the bolt has been secured into the skull 30, catheters are passed through the guide tubes 20, 21, and 22 into the bolt and through the internal passageways in the bolt into the desired positions in the brain. The guide tubes 21 and 22 may be fixed e.g. by adhesive into the upper part of the bolt. When the bolt is to be removed, the catheters are first withdrawn and the bolt is then removed by unscrewing the shank 1.

The bolt in accordance with the invention can be used to install single or multi-lumen catheters, sensors or drainage or sampling tubes into various parts of the brain, including the ventricles, sub-dural, epidural or parenchymal areas of the brain. Sampling tubes may include microdialysis catheters in which a saline solution is passed down one lumen and samples of chemicals in the brain are extracted through a second lumen via a membrane, and the extracted fluid analysed.

What is claimed is:

1. A device for accessing an interior of a skull comprising:
   (a) a cranial bolt comprising a hollow shank having a first threaded end to engage an opening in the skull and a second end; the shank defining a plurality of internal passageways; and
   (b) a plurality of tubes received and fixed within said second end of said shank;
      (i) each of said tubes communicating with a separate one of said internal passageways in the shank;
      (ii) each of the tubes comprising tubular guides through which catheters or sensors can be guided to a desired location within the skull; and
      (iii) each of the tubes including a proximal securing device to fix the catheters or sensors in said desired location.

2. A device according to claim 1 further comprising:
   (a) a flexible collar connected to the second end of the shank; the flexible collar containing said tubes.

3. A device according to claim 1 wherein:
   (a) the tubes comprise a multi-lumen catheter which is fixed in the second end of the shank;
      (i) wherein each individual lumen of the multi-lumen catheter are aligned with one of said internal passageways in the shank.

4. A device according to claim 1 wherein:
   (a) said tubes are fixed in the shank by an adhesive.

5. A device according to claim 1 further comprising:
   (a) a plastic body member receiving said shank; the plastic body member having wing-like extensions to facilitate screwing bolt into the skull.

6. A device according to claim 5 wherein:
   (a) the plastic body member is moulded on the shank.

7. A device according to claim 1 wherein:
   (a) the plurality of internal passageways defined by said shank includes:
      (i) a major passageway; and
      (ii) one or more further passageways smaller than said major passageway; said one or more further passageways being disposed around said major passageway.

8. A device according to claim 7 wherein:
   (a) the one or more further passageways are angled outwardly with respect to the major passageway.

9. A device according to claim 8 wherein:
   (a) the one or more further passageways each have a passageway axis;
   (b) the shank has a longitudinal axis; and (i) the passageway axes are inclined to the shank longitudinal axis at an angle between 3 and 15 degrees.

10. A device according to claim 1 wherein:
  (a) at least one of said tubes comprises a catheter including a sensor for assessing a desired parameter.

11. A device according to claim 1 wherein:
  (a) one or more of said tubes includes an internal reinforcing spring which imparts kink resistance.

12. A device according to claim 1 wherein:
  (a) the securing device for each of the tubes comprises a Luer lock.

13. A method for locating a catheter or sensor in an interior of a skull; the skull containing a brain; the method comprising:
  (a) cutting a hole in said skull;
  (b) fixing a cranial bolt having a hollow shank having a first end to engage an opening in the skull and a second end including a plurality of tubes in communication with passageways in the shank extending to the first end, said tubes being retained in said second end,
  (c) guiding at least one catheter or sensor through one of the tubes and through one of the passageways in the shank,
  (d) adjusting the position of the catheter or sensor relative to the bolt so as to locate a distal end of the catheter or sensor at a desired position in an interior of the brain, and
  (e) fixing said catheter or sensor at said desired position using a securing mechanism located remote from the shank.

14. A method according to claim 13 wherein:
  (a) said step of fixing said catheter or sensor at said desired position includes using a Luer lock to fix said catheter or sensor at said desired position remote from the shank.

15. A method for locating a plurality of catheters or sensors in an interior of a skull; the skull containing a brain; the method comprising:
  (a) cutting a hole in said skull;
  (b) fixing a cranial bolt having a hollow shank having a first end to engage an opening in the skull and a second end including a plurality of tubes in communication with passageways in the shank extending to the first end, said tubes being retained in said second end;
  (c) guiding a plurality of catheters or sensors through the tubes and through the passageways in the shank;
  (d) separately adjusting the position of each catheter or sensor relative to the bolt so as to locate a distal end of each catheter or sensor at a desired position in an interior of the brain; and
  (e) fixing each catheter or sensor at said desired position using a securing mechanism located remote from the shank.

16. A method according to claim 15 wherein:
  (a) said step of fixing said catheter or sensor at said desired position includes using a Luer lock to fix said catheter or sensor at said desired position remote from the shank.

* * * * *

UNITED STATES PATENT AND TRADEMARK OFFICE
CERTIFICATE OF CORRECTION

PATENT NO. : 6,623,490 B1
DATED : September 23, 2003
INVENTOR(S) : Crane et al.

It is certified that error appears in the above-identified patent and that said Letters Patent is hereby corrected as shown below:

Column 2,
Line 57, after "the" insert -- bolt, and; --

Column 3,
Line 16, delete "in situ" and insert -- *in situ* --;

Column 4,
Line 50, after "screwing" insert -- the --.

Signed and Sealed this

Ninth Day of December, 2003

JAMES E. ROGAN
*Director of the United States Patent and Trademark Office*